United States Patent [19]
Craig

[11] Patent Number: 5,935,430
[45] Date of Patent: Aug. 10, 1999

[54] STRUCTURE FOR CAPTURING EXPRESS TRANSIENT LIQUID PHASE DURING DIFFUSION BONDING OF PLANAR DEVICES

[75] Inventor: Stephen R. Craig, Wilmington, Del.

[73] Assignee: Hewlett-Packard Company, Palo Alto, Calif.

[21] Appl. No.: 09/124,107

[22] Filed: Jul. 29, 1998

Related U.S. Application Data

[63] Continuation-in-part of application No. 08/846,607, Apr. 30, 1997.

[51] Int. Cl.[6] ................................................. B01D 15/08
[52] U.S. Cl. ..................... 210/198.2; 73/61.52; 204/451; 204/601; 210/656; 422/70
[58] Field of Search ..................................... 210/635, 656, 210/659, 198.2; 204/601, 602, 603, 604, 605, 451, 452, 453, 454; 422/68.1, 69, 70; 73/61.52, 61.53

[56] References Cited

U.S. PATENT DOCUMENTS

| | | | |
|---|---|---|---|
| 3,530,568 | 9/1970 | Owczarski et al. | 29/498 |
| 3,538,744 | 11/1970 | Karasek | 73/23.1 |
| 3,678,570 | 7/1972 | Paulonis et al. | 29/498 |
| 3,732,982 | 5/1973 | Dunnill et al. | 210/198.2 |
| 4,220,276 | 9/1980 | Weisert et al. | 228/118 |
| 4,245,769 | 1/1981 | Meginnis | 228/173 B |
| 4,474,889 | 10/1984 | Terry et al. | 436/161 |
| 4,551,251 | 11/1985 | Kolobow et al. | 210/635 |
| 4,865,729 | 9/1989 | Saxena et al. | 210/198.2 |
| 4,891,120 | 1/1990 | Sethi et al. | 204/299 R |
| 4,905,497 | 3/1990 | Shindo et al. | 73/1 G |
| 4,908,112 | 3/1990 | Pace | 204/299 R |
| 4,935,040 | 6/1990 | Goedert | 55/197 |
| 5,114,551 | 5/1992 | Hjerten et al. | 204/180.1 |
| 5,116,495 | 5/1992 | Prohaska | 210/198.2 |
| 5,132,012 | 7/1992 | Miura et al. | 210/198.2 |
| 5,194,133 | 3/1993 | Clark et al. | 204/299 R |
| 5,236,118 | 8/1993 | Bower et al. | 228/193 |
| 5,453,769 | 9/1995 | Schantz et al. | 347/63 |
| 5,500,071 | 3/1996 | Kaltenbach et al. | 156/272.8 |
| 5,567,868 | 10/1996 | Craig et al. | 73/23.42 |
| 5,571,410 | 11/1996 | Swedberg et al. | 210/198.2 |
| 5,595,650 | 1/1997 | Manz | 210/198.2 |
| 5,792,943 | 8/1998 | Craig | 73/61.52 |
| 5,888,390 | 3/1999 | Craig | 210/198.2 |

Primary Examiner—Ernest G. Therkorn
Attorney, Agent, or Firm—Mark Z. Dudley

[57] ABSTRACT

A miniaturized planar device formed of first and second planar substrates that may be superimposed and diffusion bonded to form a single, planar integrated assembly. Each of the first and second planar substrates include respective component sections having respective first and second interior surfaces. One or more surface features in at least one of the first and second interior surfaces are thereby enclosed during assembly so as to form at least one corresponding internal fluid-handling feature, such as a conduit having a rectilinear, semicircular, or circular cross section. The perimeter of a surface feature is generally defined by a perimeter land which separates the surface feature from an adjacent moat. The superimposition of the first and second component sections establishes an interface between the abutted portions of the first and second interior surfaces; this interface is then subject to diffusion bonding. Diffusion bonding causes a transient liquid phase to be interposed in the interface; a flow of the transient liquid phase can correct the irregularities, asperities, or other undesired structural aspects in the abutted surfaces. Excess flow of the transient liquid phase tends to flow into the moat, wherein the excess flow may be contained, so as to thereby minimize or prevent undesirable flow of the transient liquid phase into an internal fluid-handling feature.

9 Claims, 6 Drawing Sheets

STRUCTURE FOR CAPTURING EXPRESS TRANSIENT LIQUID PHASE DURING DIFFUSION BONDING OF PLANAR DEVICES

CROSS REFERENCE TO RELATED APPLICATIONS

This application is a continuation in part of allowed application Ser. No. 08/846,607, filed on Apr. 30, 1997 in the name of Stephen R. Craig, the disclosure of which is included herein by reference. This application is related to application Ser. No. 08/845,974, now U.S. Pat. No. 5,888,390 and application Ser. No. 08/846,609, now U.S. Pat. No. 5,792,943 filed on Apr. 30, 1997 in the name of Stephen R. Craig, the disclosures of which are included herein by reference.

FIELD OF THE INVENTION

The present invention relates generally to miniaturized planar device technology and more particularly, to a land and moat structure for capturing excess flow of transient liquid phase in a diffusion bonded planar assembly.

BACKGROUND OF THE INVENTION

In certain systems that make use of planar devices having internal conduits for conveying pressurized fluids therein, smaller dimensions will generally result in improved performance characteristics and at the same time result in reduced production and analysis costs. In this regard, miniaturized planar devices provide better performance and a more compact instrument. For example, in the application of such planar devices to instruments for performing a chromatographic analysis, such miniaturized planar devices enable faster analysis, decreased sample and solvent consumption, and increased detection efficiency.

Several approaches for the miniaturization of fluid bearing conduits in miniaturized planar assemblies have developed in the art. The conventional approach provides etched planar devices on glass, silica, metal, or ceramic substrates of moderately small size. For example, planar devices may be etched in a wafer that receives a superimposed cover plate. In some approaches, certain fluid-handling functions have not been integrated in the planar device and accordingly must be effected by use of conventional devices, such as fused silica capillary tubing, that are attached to the planar device. More recent approaches have used micromachining of silicon substrates and laser ablation of organic nonmetallic substrates to provide structures of much smaller size (i.e., microstructures) on the substrate.

Micromachining techniques applied to silicon utilize a number of established techniques developed by the microelectronics industry involving micromachining of planar materials, such as silicon. Micromachining silicon substrates to form miniaturized separation systems generally involves a combination of film deposition, photolithography, etching and bonding techniques to fabricate three-dimensional microstructures. Silicon provides a useful substrate in this regard since it exhibits high strength and hardness characteristics and can be micromachined to provide structures having dimensions in the order of a few micrometers. Examples of the use of micromachining techniques to produce miniaturized separation devices on silicon or borosilicate glass chips can be found in U.S. Pat. No. 5,194,133 to Clark et al.; U.S. Pat. No. 5,132,012 to Miura et al.; in U.S. Pat. No. 4,908,112 to Pace; and in U.S. Pat. No. 4,891,120 to Sethi et al.; Fan et al., Anal. Chem. 66(1):177–184 (1994); Manz et al., Adv. Chrom. 33:1–66 (1993); Harrison et al., Sens. Actuators, B10 (2): 107–116 (1993); Manz et al., Trends Anal. Chem. 10 (5): 144–149 (1991); and Manz et al., Sensors and Actuators B (Chemical) B1 (1–6): 249–255 (1990).

A drawback in the silicon micromachining approach to miniaturization involves the chemical activity and chemical instability of silicon dioxide ($SiO_2$) substrates, such as silica, quartz or glass, which are commonly used in systems for both capillary electrophoresis (CE) and chromatographic analysis systems. Accordingly, Kaltenbach et al., in commonly-assigned U.S. Pat. No. 5,500,071, and Swedberg et al., in commonly-assigned U.S. Pat. No. 5,571,410 disclose a miniaturized total analysis system comprising a miniaturized planar column device for use in a liquid phase analysis system. The miniaturized column device is provided in a substantially planar substrate, wherein the substrate is comprised of a material selected to avoid the inherent chemical activity and pH instability encountered with silicon and prior silicon dioxide-based device substrates. More specifically, a miniaturized planar column device is provided by ablating component microstructures in a substrate using laser radiation. The miniaturized column device is described as being formed by providing two substantially planar halves having microstructures thereon, which, when the two halves are folded upon each other, define a sample processing compartment featuring enhanced symmetry and axial alignment.

Although the foregoing techniques are useful in the fabrication of miniaturized planar devices for effecting fluid-handling functions, there are significant disadvantages to the prior art approaches.

Figure 1:
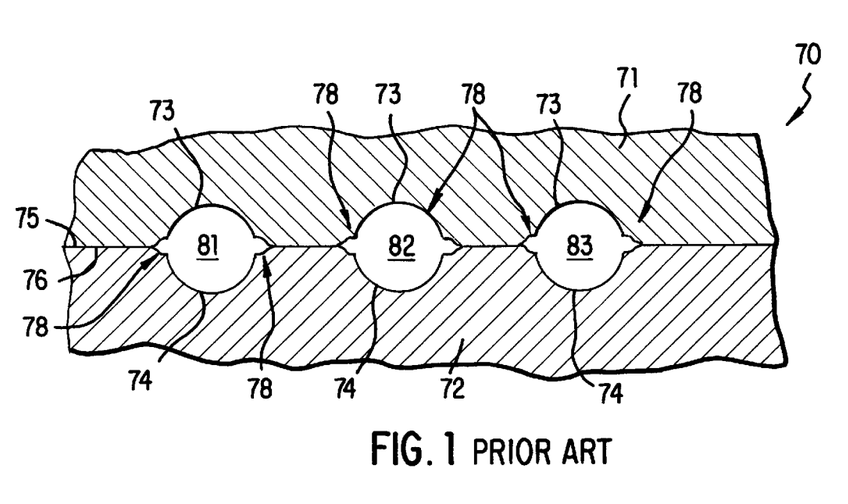
FIG. 1 is a simplified, side sectional view of a planar device incorporating fluid conduits that is constructed in accordance with the prior art.

As shown in FIG. 1, a prior art planar device 70 may be constructed to include first and second planar substrates 71, 72 each of which include spaced channels 73, 74 that are etched or otherwise formed in respective surfaces 75, 76 by conventional techniques. Superimposition and appropriate bonding of the surfaces 75,76 may succeed in adequate alignment of the channels 73, 74 such that respective fluid-handling conduits 81–83 are created. However, deficiencies in many of the conventional techniques for forming the channels 73, 74 can result in edge effects and other asperities that create undesirable defects 78 in the channels 81–83. These defects 78 retard fluid flow and create localized reservoirs of fluid; accordingly, the defects 78 degrade the efficiency and uniformity of fluid flowing in the conduits 81–83; for example, the defects 78 can degrade the separation efficiency of a conduit that is used to construct a separation column.

Another significant problem arises in the attempt to effect hermetic sealing of the superimposed surfaces 75, 76. This step is generally carried out using adhesives which may not fully isolate the conduits 81–83, thus resulting in cross-conduit leakage. Conventional surface bonds may be prone to failure, leakage, or to degradation induced by adverse conditions, such as high temperature environments, or by the destructive nature of certain gases or liquids that may be present in the conduits 81–83.

Further, silicon substrates, and most ablatable materials such as polyimides, do not offer a sufficient combination of thermal and mechanical characteristics for the substrate to be used in certain applications. For instance: silicon materials are not ductile and cannot be folded, shaped, etc.; ablatable materials exhibit a low coefficient of thermal conductivity and are not susceptible to rapid and uniform heating or cooling, nor do they offer sufficient strength or ductility such that an ablatable substrate may be configured as a connecting member, housing, or support for other components. Furthermore, ablatable materials are expressly selected for their propensity to ablate upon the application of heat, and thus are not considered to be robust and impervious to adverse (e.g., high-temperature) environments when compared to metals and metal alloys.

SUMMARY OF THE INVENTION

The present invention is directed to the construction of a miniaturized planar device formed of first and second planar substrates that may be superimposed and bonded together to form a single, planar integrated assembly. Each of the first and second planar substrates include respective component sections having respective first and second interior surfaces. The first and second planar substrates are preferably constructed to include a surface layer which exhibits the requisite thermal and mechanical characteristics such that the abutted portions of the interior surfaces of the first and second substrates may be bonded by diffusion bonding. The first and second interior surfaces are aligned, superimposed, and diffusion bonded so as to construct the planar integrated assembly. One or more surface features in at least one of the first and second interior surfaces are thereby enclosed so as to form at least one corresponding internal fluid-handling feature.

During the step of diffusion bonding, the substrates are clamped together under substantial pressure, and then heated in vacuum to a bonding temperature above the liquidus temperature of the surface layer on the component sections being bonded. The diffusion bonding causes the surface layer to melt at a selectable diffusion bonding temperature, thus forming a transient liquid phase that is interposed in the interface of the abutted portions of the first and second interior surfaces. At this temperature, the transient liquid phase fills the cracks, gaps, asperities, or other structural voids in the abutted portions. In particular, such flow will correct many of the defects that may be present in the interface of the abutted portions of the first and second interior surfaces.

In a particular aspect of the present invention, and in a departure from the prior art, the flow will correct many of the defects that may be present in the interface of first and second perimeter lands in a complementary pair of superimposed first and second surface features, thus rendering the resulting internal fluid-handling feature more useful.

In a particular aspect of the present invention, and in a departure from the prior art, the amount of transient liquid phase present in a pair of abutted perimeter lands, and thus available to correct the defects in the abutted perimeter lands, may be controlled by selecting the width of each of the abutted perimeter lands.

In another particular aspect of the present invention, and in a departure from the prior art, a moat is located so as to be adjacent to, or surround, a surface feature such that excess flow of the transient liquid phase (that is, an unwanted amount of flow of transient liquid phase from, e.g., a very wide land, or from another portion of the abutted surfaces having sufficient surface area to generate such unwanted flow) will flow into the moat, wherein the excess flow may be contained, so as to minimize or prevent the entry of excess flow into that surface feature, where it could occlude or otherwise alter the shape or dimensions of the resulting internal fluid-handling feature.

In a first preferred embodiment, the first interior surface includes a respective first surface feature and an adjacent first moat. The perimeter of the first surface feature is generally defined by a perimeter land and is separated from the moat by that perimeter land. Accordingly, the first surface feature may be covered by the second interior surface when the second planar substrate is aligned and superimposed onto the first interior surface in a controlled manner. The superimposition of the second interior surface on the uppermost surface of the perimeter land establishes a joint between the first and second interior surfaces; this joint is then subject to diffusion bonding. The first surface feature thereby is enclosed to form an internal fluid-handling feature, such as a conduit having a rectilinear or semicircular cross section.

In second preferred embodiment, a complementary pair of first and second surface features are provided respectively in the first and second interior surfaces by an etching or similar process. Each of the first and second surface features is defined by a respective perimeter land which is at least partially surrounded by a respective, adjacent moat. Accordingly, the perimeter lands of the complementary pair of surface features may be aligned in opposition and superimposed in a controlled manner, and the perimeter lands of the first and second surface features are diffusion bonded so as to establish a bond between the first and second interior surfaces, so as to combine the superimposed first and second surface features into an enclosed, internal fluid-handling feature. The first and second surface features are preferably shaped as respective first and second channels each having a semi-circular cross section. Accordingly, when one semi-circular channel is aligned and superimposed on the other semi-circular channel, a fluid-handling conduit of highly symmetrical, circular cross-section is created, which is advantageous for use as, for example, a fluid path in a fluid circuit in a sample processing or sample analysis system.

In a third embodiment of the invention, an integrated assembly may be formed by providing a single planar substrate having at least a complementary pair of first and second adjacent component sections, wherein the first and second adjacent component sections have respective first and second complementary surface features located thereon. Each of the first and second surface features is defined by a respective perimeter land which is at least partially surrounded by a respective, adjacent moat. The adjacent component sections are separated by a linear fold means. The planar substrate is composed of a ductile material in the immediate vicinity of the linear fold means, yet is generally inextensible in the component sections, such that the two adjacent component sections may be superimposed by folding the component sections upon each other about the fold axis. Upon superimposition of the component sections, the perimeter lands of the complementary pair of first and second surface features are aligned in opposition and superimposed, and the perimeter lands of the first and second surface features are diffusion bonded so as to establish a bond between the first and second interior surfaces. The superimposed first and second surface features thereby combine to form an enclosed, internal fluid-handling feature, such as a conduit having a circular cross section.

In the practice of the invention, a preferred substrate material is a metal or metal alloy, such as steel, and especially stainless steel. The preferred metal or metal alloys provide substrates that may be shaped to provide a unitary assembly having a useful configuration. Further, the preferred substrates may be produced in a variety of shapes, sizes, and configurations. Such preferred substrates are prepared for diffusion bonding by electroplating a very thin nickel-base surface layer on the component sections that are to be joined.

Particularly preferred embodiments of a surface feature include: a channel; an aperture or a combined channel and aperture; a well, notch, depression, and the like. Particularly preferred embodiments of an internal fluid-handling feature include: a conduit of semicircular, circular, or oval cross section; a bore hole, through-hole, or orifice; or a chamber or compartment.

In another particularly preferred embodiment of the invention, the aforementioned surface features are provided in a microminiature size, and therefore are described herein as microstructures. Such microstructures are ordinarily quite susceptible to occlusion when subject to even a small amount of excess flow of the transient liquid phase during the preferred process of diffusion bonding. However, in the present invention, the excess flow of the transient liquid phase is contained by an adjacent moat.

A further advantage of the present invention is that an integrated assembly having may be assembled and diffusion bonded so as to offer multiple, microminiature internal fluid-handling features in a device having a smaller volume than is possible in prior art planar devices. One preferred embodiment of the integrated assembly includes a plurality of conduits that comprise a fluid circuit that is integrated in the integrated assembly, and thus provide a great number of fluid flow paths located entirely within the integrated assembly, which is itself quite compact and amenable to construction in a variety of shapes and configurations. Because the preferred substrate material is a metal or metal alloy, it is contemplated that the integrated assembly may be easily formed in an irregular shape, such as a curved, bent, or angled configuration, so as to better conform to an irregularly-shaped, compact volume.

Also, a large number of highly miniaturized internal fluid-handling features may be integrated into an integrated assembly that heretofore would be difficult if not impossible to assemble using traditional construction techniques. Higher production yields and thus considerable cost savings and improved reliability are also realized.

Another advantage of the present invention is the use of a construction technique other than silicon micromachining techniques or silicon etching techniques to create the desired microstructures. The use of conventional metal etching processes to form microstructures in the preferred metallic substrate materials, such as metal alloys, increases the ease of fabrication and lowers the per-unit manufacturing costs in the subject devices, as compared to prior approaches, such as micromachining devices in silicon.

Preferred embodiments of the integrated assembly are quite robust, are easily cooled or heated, and are sufficiently strong and rigid so as to serve as a connecting member, support member, chassis, housing, or the like. In this regard, integrated assemblies constructed according to the invention have the added feature of being robust yet quite inexpensive, and thus may be replaced at low-cost, i.e., they have great utility in the production of disposable, miniaturized devices.

Accordingly, the subject invention finds potential application in providing planar devices having multiple internal fluid-handling features, such as fluid bearing paths or circuits, for use in fluid flow systems employed in fluidic, chemical, biological, biochemical, pharmaceutical, and medical instrumentation, processes, and the like. In one particular application, the contemplated integrated assembly may be provided in the form of a miniaturized planar separation column device for use in a sample analysis system.

DETAILED DESCRIPTION OF THE INVENTION

Before the invention is described in detail, it is to be understood that the invention is not limited to the particular component parts of the devices described or process steps of the methods described, as such devices and methods may vary. It is also to be understood that the terminology used herein is for purposes of describing particular embodiments only, and is not intended to be limiting. It must be noted that, as used in the specification and the appended claims, the singular forms "a," "an" and "the" can include plural referents unless the context clearly dictates otherwise.

In this specification and in the claims which follow, reference will be made to a number of terms which shall be defined to have the following meanings:

"Diffusion bonding" refers to a bonding technique which involves the solid-state movement of the atoms and grain growth across a joint interface. Diffusion bonding provides bonded areas which are practically indistinguishable from the adjacent parent metal even on close metallurgical examination. In this regard, reference may be made to the patent to Owczarski et al., U.S. Pat. No. 3,530,568. A particularly preferred technique of diffusion bonding has already been described herein, wherein the surfaces to be joined are initially electroplated with a very thin surface layer (e.g., approximately 0.0003 inches or less) of nickel, nickel-phosphorous, or a nickel-cobalt alloy. The preferred diffusion bonding process for the integrated assembly may be understood to include heating the assembly in a vacuum (approximately $10^{-5}$ torr) to the desired bonding temperature above the liquidus temperature of the nickel-base surface layer on the component sections being bonded (typically in the range of 900–1000 degree(s) F.) At this temperature the surface layer melts and a thin layer of liquid alloy wets and fills the gaps and other asperities (see, for example, asperities 78 in FIG. 1) between any abutted surfaces. While the assembly is held at temperature, rapid diffusion of certain alloying elements occurs between the molten alloy and the base metal, resulting in a compositional change at the joint. This change raises the local melting point and causes the joint to isothermally solidify, thus creating the initial bond. Upon completion of the initial isothermal solidification (typically in 1–3 hours), the joint microstructure resembles that of the base metal except for some compositional and structural heterogeneity. Additional steps may optionally be employed in continuation of the heat treatment at temperature for a time sufficient to completely homogenize the joint region so that, ultimately, it reaches a composition corresponding or at least closely equivalent to the base metal, although a separate and distinct subsequent heat treatment may be utilized. After completion of the bonding process, the bonded assembly can then be given whatever further heat treatments are required for strengthening or in fulfillment of coating requirements.

"Surface feature" refers to a structural feature on an interior surface of a component section of a substrate that is a precursor to formation of an internal fluid-handling feature and is typically distinguishable as from the immediately surrounding portion of the component section by way of a perimeter land. Examples of a surface feature include an: aperture, recess, perforation, orifice, groove, chamber, compartment, depression, channel, pad, block, protrusion, nipple, or predefined region having a surface treatment. Note that the shape, dimensions, and symmetry of the various surface features contemplated herein will vary according to the implementation of the invention.

"Interior surface" refers to a surface having on a portion thereof a surface layer suited for diffusion bonding, that is, a surface layer composed of an alloy that is formulated to melt at a temperature at which the base metal (in the foldable substrate) can be exposed without deleterious effect; the surface layer must be of a composition and thickness such that solidification will occur at a desired temperature, and be chemical and microstructural homogeneity of the bond may be achieved in a practical processing time. Various melting point depressants such as phosphorous, boron, silicon, manganese, columbium and titanium are possible. Several combinations of these elements with nickel produce surface layers with satisfactory melting points. However, as disclosed in U.S. Pat. No. 3,678,570, some depressants except boron may produce unwanted stable phases at the joint interface. Satisfactory bonds have been obtained between component sections in a foldable substrate formed of 316L stainless steel utilizing the foregoing process parameters and a surface layer of nickel-phosphorous alloy on the component sections. The resulting bond lines were found to be nearly indistinguishable; more importantly, the asperities in the edges at joints between superimposed channels were filled and accordingly indistinguishable, even after transversely sectioning the integrated assembly and subjecting the sectioned channels to microscopic analysis.

"Fluid-handling" and "fluid-handling functions" include reference to the initiation, distribution, redirection, termination, control, detection, analysis, sensing, treatment, and similar functions with respect to one or more fluid streams. Hence, the present invention will find particular application in a variety of fluid systems that benefit from an integrated assembly that supports one or more fluid-handling functions with respect to one or more fluid streams.

"Surface treatment" is used to refer to preparation or modification of a portion of a component section, and in particular of an interior surface of a channel which will form a conduit to be subjected to a sample fluid, whereby the characteristics of the surface are altered or otherwise enhanced. Accordingly, "surface treatment" as used herein includes: physical surface coatings such as silication or silane coatings; physical surface adsorptions; covalent bonding of selected moieties to functional groups on the surface of channel substrates; methods of coating surfaces, including dynamic deactivation of channel surfaces, substrate grafting to the surface of channel substrates, and thin-film deposition of materials such as diamond or sapphire to channel substrates.

"Land" refers to a raised structural feature, located in an interior surface of a component section, and having a sufficient height from the immediately surrounding portion of the component section such that a land on a first component section may abut a corresponding portion of an interior surface of a second component section, when such first and second component sections are arranged in opposition and superimposed. Preferably, a land defines the perimeter of a selected surface feature so as to separate that surface feature from an adjacent moat.

"Moat" refers to a structural feature located in a component section, wherein the moat has sufficient depth with respect to the portion of the component section that is immediately adjacent the moat, such that an excess flow of transient liquid phase from the adjacent portion of the component section tends to flow into the moat.

"Microstructure" refers to a surface feature having dimensions on the order of approximately 5 to 5000 micrometers and may include a microchannel, microaperture, microdepression, and the like. Microstructures in the form of microchannels of a semi-circular cross section may be successfully etched by controlling the etch process. When a first microchannel is aligned with a second microchannel thus formed, a miniaturized fluid-handling conduit of highly symmetrical circular cross-section is defined. Note that the shape, dimensions, and symmetry of the various microstructures contemplated herein will vary according to the implementation of the invention.

"Microalignment" as used herein refers to precise alignment of structures, microstructures, and other surface features, including: the enhanced alignment of apertures, complementary channels, or compartments with each other; of inlet and/or outlet ports with channels or separation compartments; of detection means with ports, channels or separation compartments; and of detection means with other detection means, and the like. The precision in microalignment contemplated in the practice of the invention is believed to be on the order of less than one to two micrometers of error.

"Linear fold means" refer to means for dividing a single substrate into at least first and second component sections whereby the operation of the linear fold means allows microalignment of complementary surface features in the first and second component sections. Linear fold means can be formed in the substrate either by etching, or by other methods of fabricating shaped apertures or depressions. Representative linear fold means that can be employed herein include a plurality of co-axially arranged apertures in component parts and/or a plurality of corresponding features in the substrate, e.g., depressions, grooves, slots, tunnels, hollow ridges, or the like. The preferred microalignment of two or more component sections is effected by forming at least one linear fold means provided between adjacent pairs of component sections, such that each pair of the component sections have surfaces that can be folded to overlie each other thereby forming composite micro-scale features such as apertures, compartments, or channels. Such linear fold means is preferably embodied by a row of spaced-apart perforations etched in a particular substrate, or by spaced-apart slot-like depressions or apertures etched so as to extend only part way through the substrate. The perforations or depressions can have circular, diamond, hexagonal or other shapes that promote hinge formation along a predetermined straight line. The linear fold means preferably includes a "fold relief" which refers to a relief or similar excision of the substrate that facilitates folding of the substrate and the subsequent microalignment of the microstructures while maintaining the inextensibility of the substrate. The fold relief is effective at relieving the stress or deformation induced in the substrate in the immediate area of the fold axis by the folding motion.

"Foldable substrate" refers to a substrate which includes linear fold means, at least first and second component sections so defined by the linear fold means, and a characteristic of being foldable about the fold axis such that the substrate material is substantially inextensible in the direction generally transverse to the fold axis. As a result, the microalignment of surface features upon closure of the component sections is maintained due to the lack of extension of the foldable substrate.

"Substantially inextensible" is used herein to refer to a characteristic physical nature of a foldable substrate material that resists extension from the fold axis when the foldable substrate is subject to the typical forces which it is expected to receive during the assembly and use of an integrated assembly. Accordingly, miniaturized column devices are formed herein using suitable substrates which exhibit inextensibility when folded, such as metals and metal alloy substrates.

"Etched" and "etching" refer to surface material removal processes, but also include known machining or cutting processes. Etching is a preferred method for forming surface features in a wide variety of geometries. Any geometry which does not include undercutting may be provided using etching techniques. As mentioned, other forming methods for providing surface features are also included, such as drilling, coining, fine blanking, milling, and abrading (using an abrasive in, e.g., an air or water stream.) Etching can include such processes as common photolithography wherein surface features may be formed by imaging a lithographic mask onto a suitable substrate and then etching the substrate in areas that are unprotected by the lithographic mask. Such masks may define all of the etched features for a selected area of the substrate, for example, and the pattern may encompass multiple pairs of component sections to be created on the substrate, each of which feature complementary sets of microstructures. Alternatively, individual patterns such as an aperture pattern, a channel pattern, etc., may be placed side by side on a common mask for stepwise exposure of large substrates which are eventually processed to produce a plurality of individual substrates. An etching system employed in the invention generally includes beam delivery optics, alignment optics, a high precision and high speed mask shuttle system, and a processing chamber including mechanism for handling and positioning the substrate material.

"Optional" or "optionally" means that the subsequently described feature or structure may or may not be present in the embodiment been described, or that the subsequently described event or circumstance may or may not occur, and that the description includes both instances where said feature or structure is present and instances where the feature or structure is absent, or instances where the event or circumstance occurs and instances where it does not.

"Robust" refers to a desirable characteristic of a device that exhibits an ability to perform as expected while withstanding adverse environments, mishandling, and operation at an elevated temperature.

Referring generally to FIGS. 2–7, and as will be appreciated by those working in the field of planar devices, the invention described herein may be understood to provide a wide variety of miniaturized integrated assemblies having internal fluid-handling features suitable for effecting one or more respective fluid-handling functions. In the general practice of this invention, a first component section may be arranged in opposition with a second component section and, in combination with suitable positioning means (which includes but it is not necessarily limited to the fold means disclosed herein), the first component section is superimposed on the second component section. A surface feature, or a pair of surface features, or a pair of complementary microstructures therein, will then form an enclosed internal fluid-handling feature, such as a conduit, channel, or compartment. In particular, one or more lands which respectively defined a first surface feature, or a pair of surface features, are joined as abutted portions of the first and second component sections, and are diffusion bonded to form a gas- or liquid-tight seal.

It will therefore be readily appreciated that an exemplary internal fluid-handling feature may be constructed in the form of a conduit capable of bearing a pressurized fluid stream between first and second spaced ports or apertures, that is, between ports or apertures or other surface features that are physically separated and which communicate with an exterior surface of the integrated assembly. It will also be appreciated that the surface features (that serve as precursors to a conduit) preferably take the form of a complementary pair of open channels, which when superimposed are sized and shaped to form the preferred conduit. Although the channels illustrated herein are represented in a generally extended form, other channel shapes may be etched in a large variety of other configurations, such as in a curved, undulating, serpentine, spiral, or any tortuous path desired. Further, as described in greater detail below, a channel may be formed in a wide variety of channel geometries and cross sections including semi-circular, rectilinear, rhomboid, and the like, and the channels may be formed in a wide range of aspect ratios. It is also noted that a device having a variety of apertures, ports, and the like, some of which are in fluid communication with one or more channels or other surface features, and some of which are not in fluid communication with a channel or other surface features, will fall within the spirit of the present invention.

Figure 6:
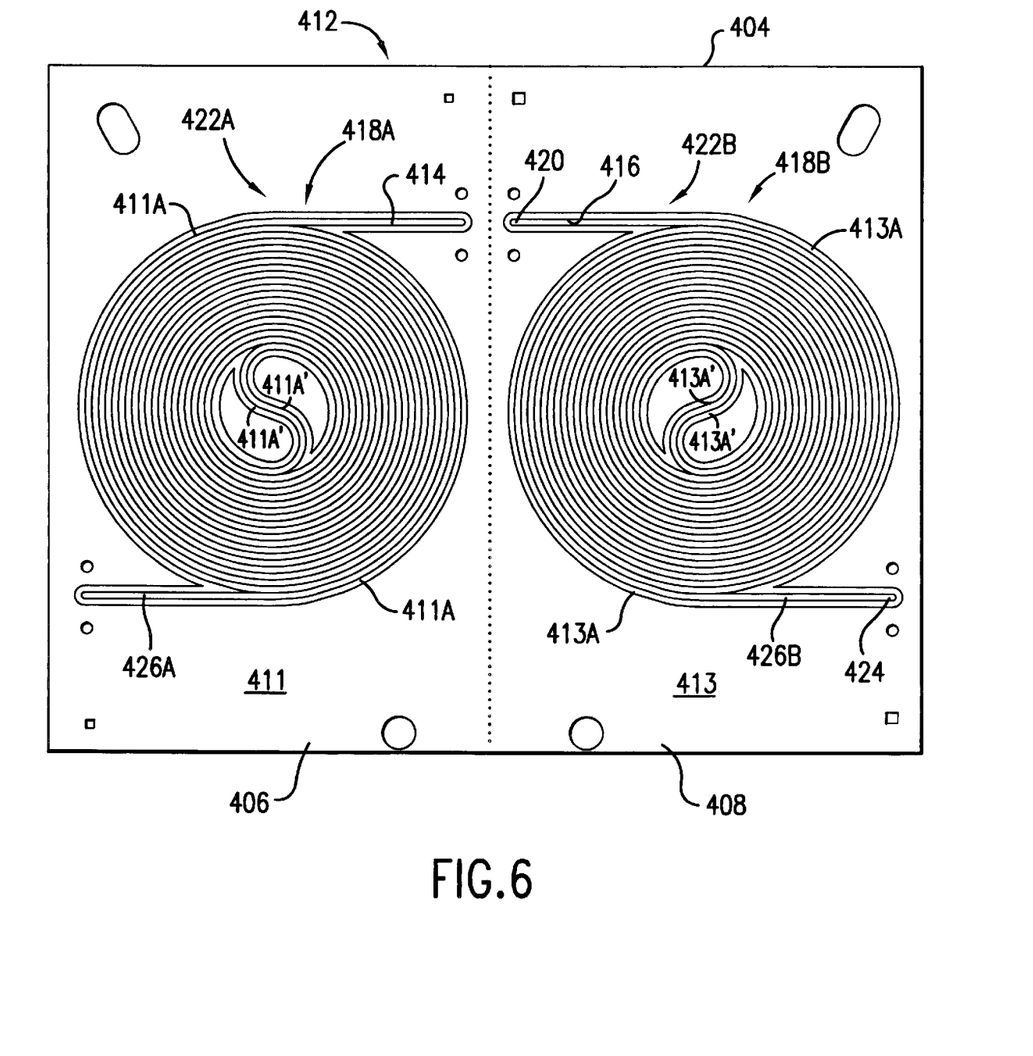
FIG. 6 is a plan view of first and second interior surfaces, prior to closure, of a foldable substrate which will form a planar separation column device.
Figure 7:
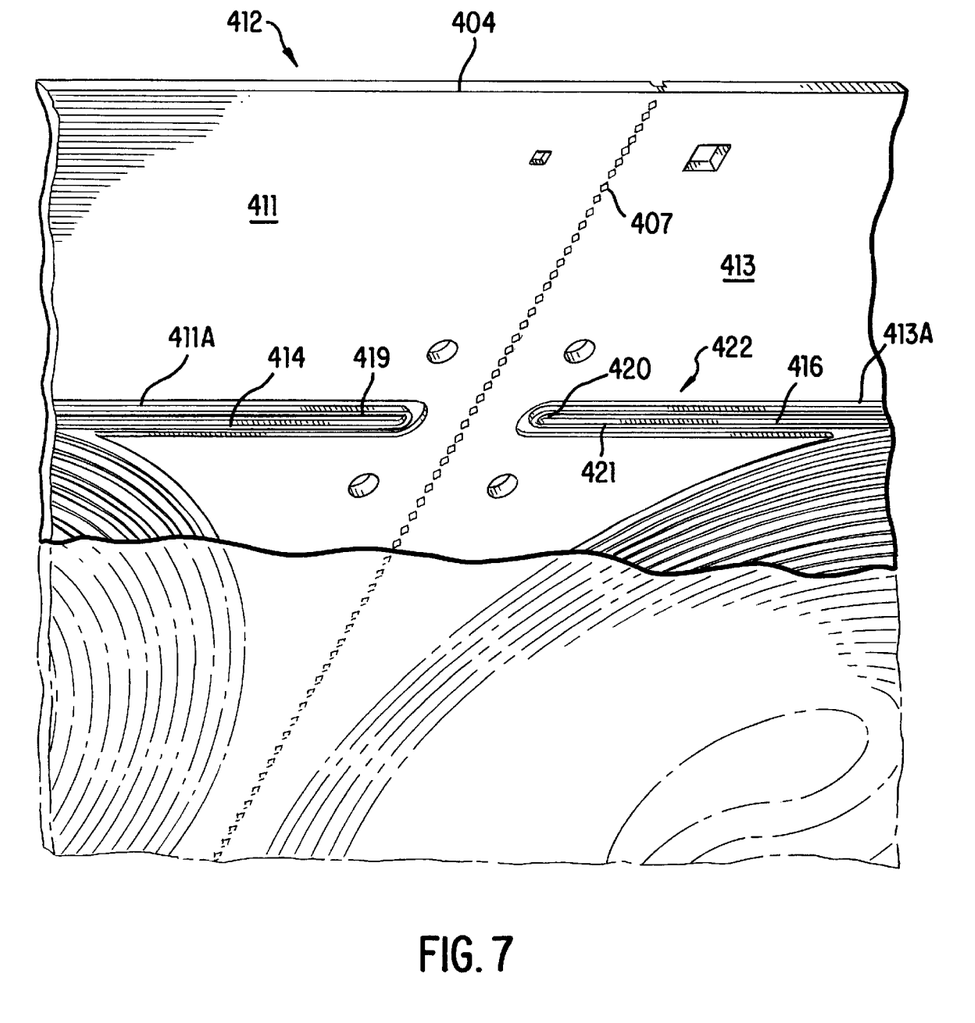
FIG. 7 is a side perspective view showing in detail a portion first and second interior surfaces of the foldable substrate of FIG. 6.

Hence, another exemplary fluid-handling feature includes one or more apertures provided so as to communicate with a channel or compartment at a first end thereof to form an inlet port, thus enabling the entry of fluid from an external source into the channel or compartment. A second aperture may be provided for fluid communication with the channel or compartment at a second end thereof so as to form an outlet port, thus enabling passage of fluid from the channel or compartment to an external receptacle. Accordingly, a miniaturized separation column device may be formed having a flow path extending from the first end of a sample processing compartment and passing to the second end thereof, whereby analysis of samples may be carried out using techniques well known in the art. An exemplary separation column device is represented in FIGS. 6-7. Alternatively, a miniaturized planar manifold may be constructed as illustrated in FIG. 5 to include internal fluid-handling features provided in the form of conduits, apertures, and the like, wherein the planar manifold includes one or more apertures provided so as to communicate with a channel or compartment at various points to form an array of inlet ports and outlet ports, thus enabling the delivery of fluid from an external source to and from the conduit or compartment.

Figure 2:
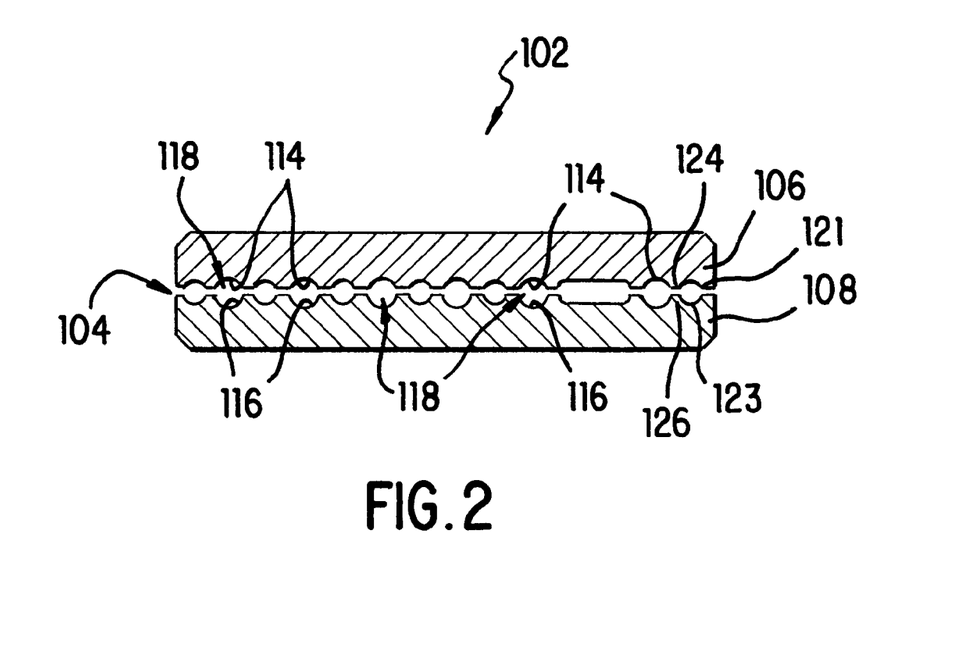
FIG. 2 is a cross-sectional axial view of conduits formed by the alignment of a complementary pair of surface features provided in the form of semi-circular channels, via superimposition of first and second component sections, in a first embodiment of an integrated assembly constructed according to the present invention.
Figure 3:
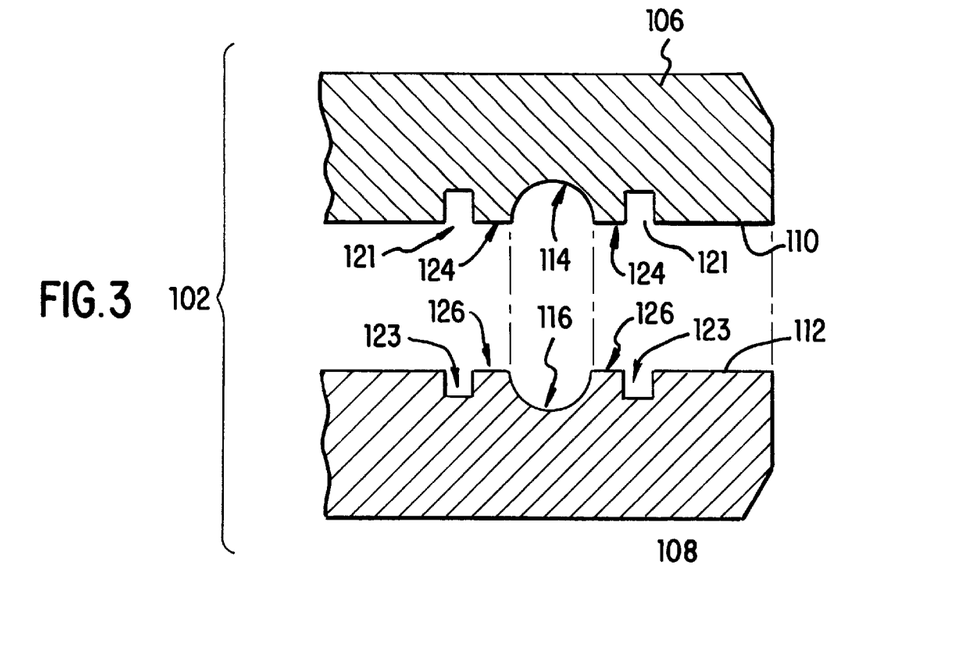
FIG. 3 is a cross-sectional axial view of a conduit defined by perimeter lands and having adjacent moats, found in the integrated assembly of FIG. 2.

Referring now to FIGS. 2-3, a first embodiment of an integrated assembly for performing one or more of a wide variety of fluid-handling functions is formed as a miniaturized planar device 102 by providing an interface 104 interposed between first and second component sections indicated at 106 and 108 respectively. The device 102 may be constructed from first and second substantially planar substrates each of which include first and second component sections 106 and 108 which have substantially planar interior surfaces, indicated at 110 and 112 respectively, which have surface features, microstructures, or other miniaturized structures etched therein. More particularly, a first channel pattern 114 is etched in the first planar interior surface 110 and a second, complementary channel pattern 116 is etched in the second planar interior surface 112. Located immediately adjacent to each channel in the channel pattern 114 is at least one moat 121 that is separated from its respective channel by a perimeter land 124. Located immediately adjacent to each channel in the channel pattern 116 is at least one moat 123 that is separated from its respective channel by a perimeter land 126. Accordingly, each channel is at least partially defined by its respective perimeter land. The first and second channel patterns 114,116 are respectively etched in the first and second component sections 106 and 108 in opposing locations, such that the first and second channel patterns 114,116 are made to be the mirror image of each other. The first and second component sections 106 and 108 may then be superimposed and the abutted portions of the first and second planar interior surfaces 110,112 (and, in particular, the abutted perimeter lands 124,126) are diffusion bonded to form the desired internal fluid-handling features 118. In the illustrated planar device 102, the resulting internal fluid-handling features 118 take the form of elongated conduits each having a circular cross section.

Figure 4:
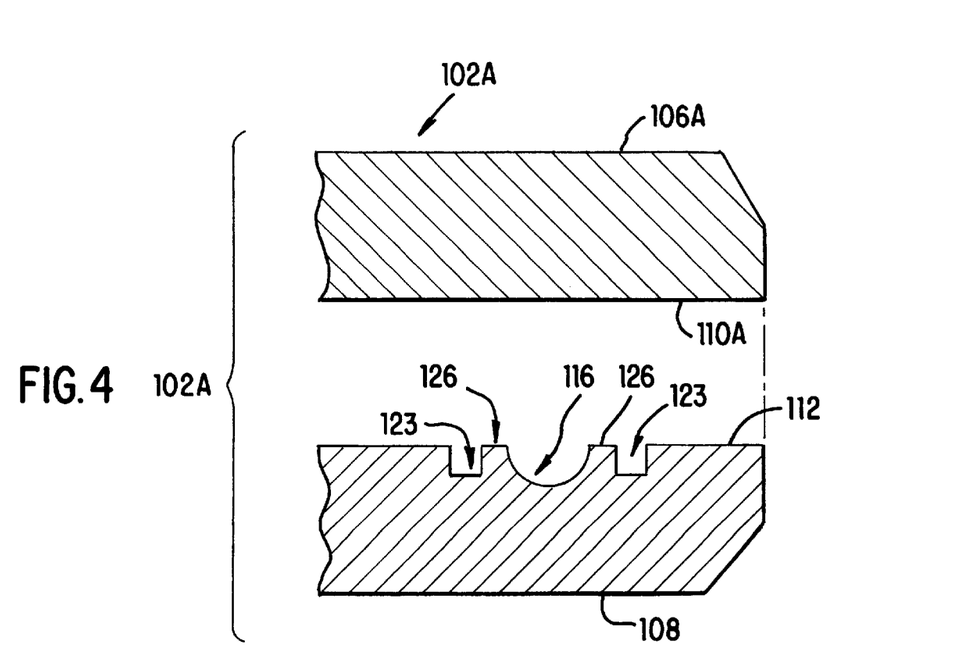
FIG. 4 is a cross sectional axial view of a conduit having semi-circular cross section found in an alternative embodiment of the integrated assembly of FIG. 2.

Referring now to FIG. 4, a second, alternative embodiment of an integrated assembly for performing one or more of a wide variety of fluid-handling functions is formed as a miniaturized planar device 102A by providing first and second component sections indicated at 106A and 108 respectively. The first component section 106A lacks the channel pattern 114 and moat 121 illustrated in FIG. 3 and thus functions simply as a cover plate. In the illustrated planar device 102A, the resulting internal fluid-handling feature is formed as an elongated conduit having a semi-circular cross section.

Figure 5:
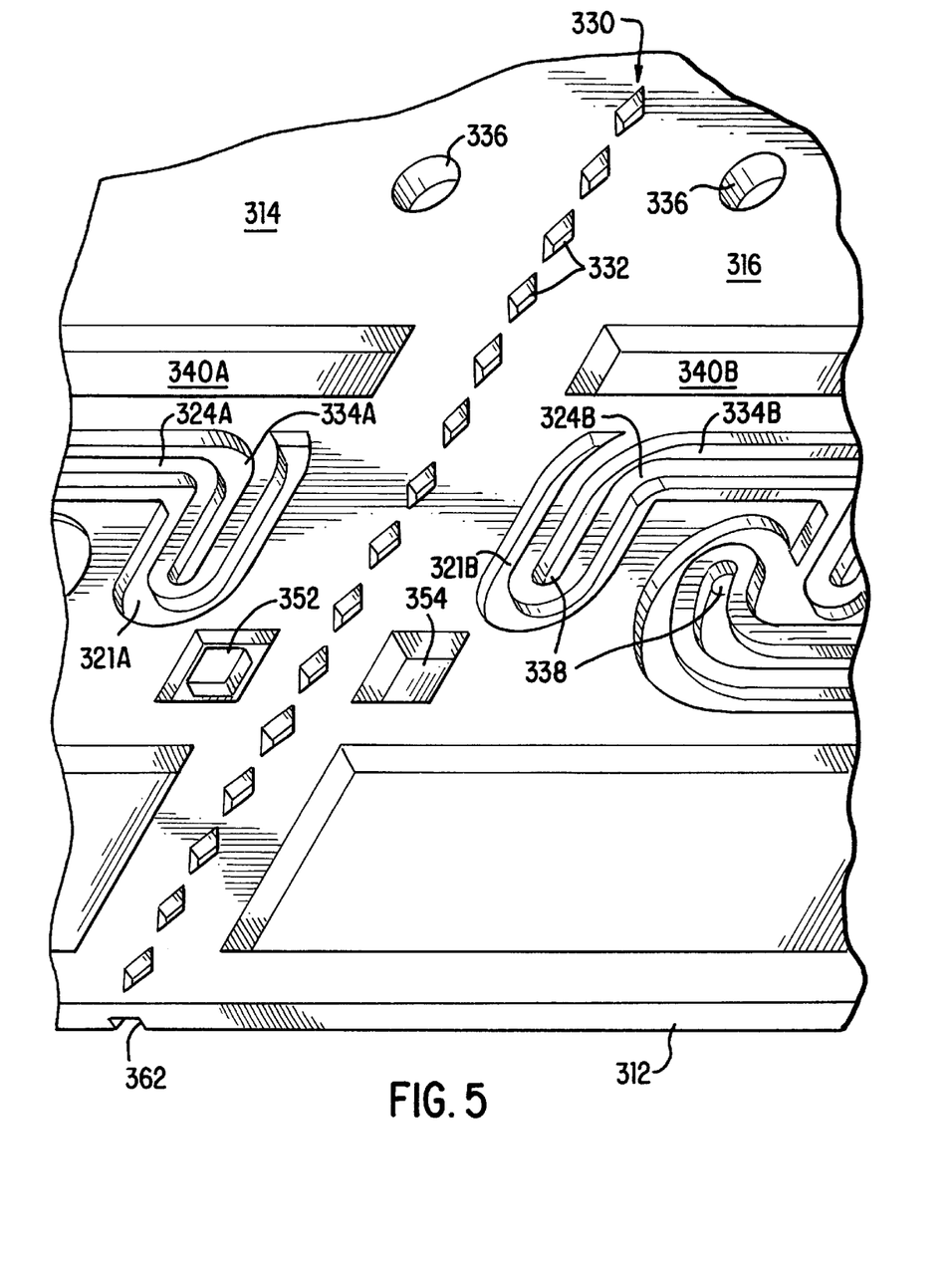
FIG. 5 is a side perspective view showing in detail a portion of an interior surface of a component section of a substrate prior to formation of a planar manifold device.

As illustrated in FIG. 5, a miniature planar manifold device may be provided in another embodiment of an integrated assembly formed from a foldable substrate 312. The foldable substrate 312 includes first and second component sections 314, 316 and a variety of etched microstructures, including: a linear fold means 330 including a linear arrangement of spaced perforations 332; device mounting holes 336; a variety of apertures 338; complementary microstructures such as channels 334A and 334B; thermal breaks 340A, 340B; and microalignment corroboration means in the form of blocks 352 and windows 354. The linear fold means 330 further includes a preferred embodiment of a fold relief constructed in the form of a groove 362 which underlies the perforations 332. Located immediately adjacent to each channel 334A, 334B is at least one moat 321A, 321B that it is located between a perimeter land 324A, 324B and a portion of the component sections 314, 316 having a substantial surface area. Accordingly, the excess transient liquid phase that accumulates on that portion of the component sections 314,316 can flow into one or more of the moats 321A 321 B, where it is contained, and thereby prevented from entering the channels 334A, 334B.

As illustrated in FIGS. 6–7, a miniaturized separation column may be provided in another embodiment of an integrated assembly formed from a foldable substrate 412. In the practice of the invention, a miniaturized planar column device may be formed by etching a set of specialized features in a foldable substrate 412 to form complementary microstructures. For example, the foldable substrate 412 for a miniaturized separation column includes complementary microstructures having micro-capillary dimensions ranging from 50–800 micrometers in diameter and path lengths of up to 15 meters or greater. A sample processing compartment may then be provided in the form of a separation column formed by superposition of complementary microstructures 418A, 418B. The sample processing compartment includes an elongate bore defined by the first and second complementary channels 414 and 416. The sample processing compartment may be formed by folding the first and second component sections 406 and 408 in facing abutment with each other about a fold axis defined by a linear fold means in the form of a linear arrangement of perforations 407. In the practice of the invention, the abutted portions of the surfaces 411, 413 may be diffusion bonded to form a fluidtight sample processing compartment.

It is further contemplated to etch the first and second channels 414 and 416 so as to have semi-circular cross-sections whereby alignment of the component sections 406, 408 defines a sample processing compartment 418 having a highly symmetrical circular cross-section to enable enhanced fluid flow therethrough; however, as discussed above, a wide variety of channel geometries are also within the spirit of the invention. It is particularly contemplated to form the mating surfaces 411, 413 to include a surface layer of nickel alloy that melts at the diffusion bonding temperature so as to provide a transient liquid phase, so as to promote the filling of surface defects, as already described.

In a particular feature of the invention, a pair of complementary outer moat channels 411A, 413A and a pair of complementary inner moat channels 411A', 413A' surround the lands 419, 421 which respectively define first and second channels 414 and 416 in outermost and innermost portions of the compartments 418A, 418B. The first and second channels 414 and 416 preferably include semi-circular cross-sections whereby alignment of the component sections 406, 408 defines a sample processing compartment having a highly symmetrical circular cross-section to enable enhanced fluid flow therethrough. In this manner, the first and second component sections 406 and 408 may be diffusion bonded together without excess transient liquid phase overflowing into the channels 414 and 416 from the nearby portions of the surfaces 411, 413. The result is a planar capillary separation device defined by the superposition of the channels 414, 416 and a liquid-tight, diffusion-bonded weld. The planar capillary separation device has the same thermal properties and the same mechanical strength as the bulk foldable substrate material. As a result, the planar capillary separation device is especially susceptible to uniform heating and cooling, which can be a benefit when effecting a chromatographic sample analysis.

The miniaturized column device 402 further comprises means for communicating associated external fluid-handling functional means (not shown) with the sample processing compartment to provide a sample analysis device. More particularly, a plurality of apertures may be etched in the foldable substrate, wherein said apertures extend from at least one exterior surface of the support body and communicate with at least one channel, said apertures permitting the passage of fluid therethrough. In this regard, an inlet port 420 may be etched in the second component half 408 and communicate with a first end 422A, 422B of the first and second channel 414, 416. In the same manner, an outlet port 424 may be etched in the second component half 408 and communicate with a second end 426A, 426B of said first and second channels 414, 416. As is readily apparent, a capillary column may thereby be formed by superposition of channels 414, 416, having a flow path extending from the first end 422A, 422B to the second end 426 thereof, by communicating fluids from an associated source (not shown) through the inlet port 420, passing the fluids through the sample processing compartment formed by the alignment of channels 414 and 416, and allowing the fluids to exit the sample processing compartment via the outlet port 424. In this manner, a wide variety of analysis procedures may be carried out in the subject miniaturized column device using techniques well known in the art.

What is claimed is:

1. An integrated assembly, comprising:

first and second planar substrates, each of the first and second planar substrates having respective component sections and having respective first and second interior surfaces, each of the first and second interior surfaces having a respective surface layer;

a first surface feature in at least one of the first and second interior surfaces, the perimeter of the first surface feature being generally defined by a first perimeter land;

an adjacent moat separated from the surface feature by the perimeter land;

the second planar substrate being aligned and superimposed onto the first interior surface in a controlled manner such that the first surface feature is covered by the second interior surface to form an internal fluid-handling feature, and wherein the abutted portions of the surface layers of the first and second substrates being subject to diffusion bonding; and wherein an excess flow of transient liquid phase is contained in the first moat, so as to thereby minimize excess flow of the transient liquid phase into the internal fluid-handling feature.

2. The integrated assembly of claim 1, further comprising a second surface feature in the alternative one of the first and second interior surfaces, the perimeter of the second surface feature being generally defined by a second perimeter land, and wherein the first and second perimeter lands are joined and diffusion bonded to form the internal fluid-handling feature.

3. The integrated assembly of claim 2, wherein the first and second surface features further comprise complementary microstructures.

4. The integrated assembly of claim 2, wherein the internal fluid-handling feature is a conduit.

5. The integrated assembly of claim 2, wherein the conduit further comprises a surface treatment, whereby the conduit functions as a separation column.

6. The integrated assembly of claim 2, wherein the first and second planar substrates further comprise a metal alloy substrate material prepared for diffusion bonding by electroplating a nickel-base surface layer on the portions of the component sections that are to be subject to diffusion bonding.

7. The integrated assembly of claim 1, wherein the surface feature further comprises a semi-circular channel.

8. The integrated assembly of claim 1, wherein the surface feature further comprises a rectilinear channel.

9. The integrated assembly of claim 1, wherein the adjacent component sections are separated by a linear fold means and the planar substrate is composed of a ductile material in the immediate vicinity of the linear fold means, and is generally inextensible in the component sections, such that the two adjacent component sections may be superimposed by folding the component sections upon each other about the fold axis.

* * * * *

UNITED STATES PATENT AND TRADEMARK OFFICE
CERTIFICATE OF CORRECTION

PATENT NO. : 5,935,430
DATED : 08/10/99
INVENTOR(S) : Stephen R. Craig

It is certified that error appears in the above-indentified patent and that said Letters Patent is hereby corrected as shown below:

On the title page, item [54],
    In the title, first line, the word "express" should read
-- excess --

Signed and Sealed this

First Day of February, 2000

Attest:

Q. TODD DICKINSON

Attesting Officer     Acting Commissioner of Patents and Trademarks